US008273732B2

(12) United States Patent
Chaudhary

(10) Patent No.: US 8,273,732 B2
(45) Date of Patent: Sep. 25, 2012

(54) COMPOSITIONS FOR COMBATING BETA-LACTAMASE-MEDICATED ANTIBIOTIC RESISTANCE USING BETA-LACTAMASE INHIBITORS USEFUL FOR INJECTION

(75) Inventor: Manu Chaudhary, Haryana (IN)

(73) Assignee: Venus Remedies Limited, Panchkula-Haryana (IN)

( * ) Notice: Subject to any disclaimer, the term of this patent is extended or adjusted under 35 U.S.C. 154(b) by 1260 days.

(21) Appl. No.: 11/720,710

(22) PCT Filed: Nov. 28, 2005

(86) PCT No.: PCT/IN2005/000382

§ 371 (c)(1),
(2), (4) Date: Jun. 1, 2007

(87) PCT Pub. No.: WO2006/059344

PCT Pub. Date: Jun. 8, 2006

(65) Prior Publication Data

US 2010/0160277 A1   Jun. 24, 2010

(30) Foreign Application Priority Data

Dec. 2, 2004 (IN) .......................... 2411/DEL/2004

(51) Int. Cl.
*A61K 31/43* (2006.01)
(52) U.S. Cl. ..................................................... 514/192
(58) Field of Classification Search .................. None
See application file for complete search history.

(56) References Cited

U.S. PATENT DOCUMENTS

2003/0078418 A1* 4/2003 Balkovec et al. ............... 544/59

OTHER PUBLICATIONS

Crosby et al (Antimicrob Agents Chemother 22:398-405, 1982).*
Fantin et al (Antimicrob Agents Chemother 34:581-586, 1990).*
UNASYN® pamphlet (dated Jun. 11, 2001).*
Rodriguez, et al., Phenotypic Confirmation of Extended-Spectrum B-Lactamases (ESBL) in Clinical Isolates of *Escherichia coli* and *Klebsiella pneumoniae* at the San Juan Veterans Affairs Medical Center, Puerto Rico Health Sciences Journal, Sep. 2004, p. 207-215, vol. 23, No. 3, University of Puerto Rico Medical Sciences Campus, Puerto Rico.
Jacoby, Genetics of Extended-Spectrum Beta-Lactamases, European Journal of Clinical Microbiology & Infectious Diseases,1994, p. S2-S11, vol. 13, suppl. 1, Springer, Germany.
Niemeyer, Regulation of Beta-Lactamase Induction in Gram-Negative Bacteria: A Key to Understanding the Resistance Puzzle, Military Medicine, Dec. 1994, p. 732-735, vol. 159, No. 12, Association of Military Surgeons, United States, USA.
Danziger, et al., Bacterial Resistance to Beta-Lactam Antibiotics, American Journal of Health-System Pharmacy, Mar. 1995, p. S3-S8, vol. 52, suppl. 2, American Society of Health-System Pharmacists, USA.
Medeiros, Evolution and Dissemination of Beta-Lactamases Accelerated by Generations of Beta-Lactam Antibiotics, Clinical Infectious Diseases, 1997, p. S19-S45, vol. 24, suppl. 1, The University of Chicago Press, USA.
Ritter, et al., Outbreak of a Nosocomial Infection of SHV2-Beta-Lactamase-Containing *Klebsiella pneumonia* Strains in an Operative Intensive Care Unit, Immunitat and Infection, 1992, p. 3-6, vol. 20, No. 1, Richard Pflaum Verlag, Germany. (English Abstract Only).
Cavalieri, Influence of Beta-Lactamase Inhibitors on the Potency of Their Companion Drug with Organisms Possessing Class I Enzymes, Antimicrobial Agents and Chemotherapy, 1991, p. 1343-1347, vol. 35, No. 7, American Society for Microbiology, USA.
Ghatole, et al., Correlation of Extended Spectrum Beta-Lactamases Production with Cephalosporin Resistance in Gram Negative Bacilli, Indian Journal of Pathology & Microbiology, 2004, p. 82-84, vol. 47, No. 1, Indian Journal of Pathologists and Microbiologists, India.
Lopez-Hernandez, et al., In Vitro Activity of Beta-Lactam Agents and Beta-Lactamase Inhibitors in Clinical Isolates of *Acinetobacter baumannii*, Revista Espanola de Quimioterapia, Jun. 1999, p. 140-143, vol. 12, No. 2, J.R. Prous, S. A., Spain. (English Abstract Only).
Finegold, In Vitro Efficacy of Beta-Lactam/Beta-Lactamase Inhibitor Combinations Against Bacteria Involved in Mixed Infections, International Journal of Antimicrobial Agents, 1999, p. S9-S14, vol. 12, suppl. 1, Elsevier Science Publishers, Netherlands.
Fantin B et al., Activity of Sulbactum in combination with ceftriaxone in-vitro and in Experimental Endocarditis Caused by *Escherichia coli* Producing SHV-2-Like B-Lactamase, Antimicrobial Agents and Chemotherapy, Apr. 1990, p. 581-586, vol. 14, No. 4, American Society for Microbiology.
Pfizer, Fachinformation: UNACID, internet article, Mar. 2000.

* cited by examiner

*Primary Examiner* — Craig Ricci
(74) *Attorney, Agent, or Firm* — Morgan Lewis & Bockius LLP

(57) ABSTRACT

The invention describes a composition for combating beta-lactamase-mediated antibiotic resistance using beta-lactamase inhibitor useful for injection, capable of pharmaceutical application. The invention relates to pharmaceutical composition containing ceftriaxone (normally as ceftriaxone sodium) and sulbactam (normally as sulbactam sodium). Such compositions are found to be useful for intramuscular or intravenous administration as antibiotics for hospitalized patients with serious infections. Specifically, this invention relates to a pharmaceutical composition further including an aminocarboxylic acid chelating agent, for example, ethylenediaminetetraacetic acid (EDTA), or a pharmaceutically acceptable salt thereof. The pharmaceutical compositions of this invention have been found normally to enhance resistance to particulate formation in solutions to be administered parenterally. The invention also gives details of the dosage forms stored in sealed containers to be reconstituted before use. The invention also gives a process to manufacture these compositions. The invention gives a method of treating a subject having a condition or disorder, wherein a treatment with ceftriaxone sodium and sulbactam sodium is indicated.

9 Claims, No Drawings

COMPOSITIONS FOR COMBATING BETA-LACTAMASE-MEDICATED ANTIBIOTIC RESISTANCE USING BETA-LACTAMASE INHIBITORS USEFUL FOR INJECTION

FIELD OF THE INVENTION

The invention relates to pharmaceutical compositions containing ceftriaxone (normally as ceftriaxone sodium) and sulbactam (normally as sulbactam sodium) commercially available as ceftriaxone sodium and sulbactam sodium. Such compositions are found to be useful for intramuscular or intravenous administration as antibiotics for hospitalized patients with serious infections specifically due to beta lactamase producing bacterial strains. This invention relates to a pharmaceutical compositions further including an aminocarboxylic acid chelating agent, for example, ethylene diamine tetraacetic acid (EDTA), or a pharmaceutically acceptable salt thereof. The pharmaceutical compositions described herein normally have been found to enhance resistance to particulate formation in solutions to be administered parenterally.

BACKGROUND OF THE INVENTION

There have been increased incidence of bacterial resistance to beta lactam antibiotics in the past 15 years, in spite of the introduction of potent new antibacterial agents belonging to novel 25 chemical classes such as penems, cephems, oxacephems, monobactams, and carbaphenems.

Del Carmen Rodriguez M., et. al. (2004), in their paper, "Phenotypic confirmation of extended-spectrum beta-lactamases (ESBL) in clinical isolates of *Escherichia coli* and *Klebsiella pneumoniae* at the San Juan Veterans Affairs Medical Center", have discussed about ESBLs as an important mechanism of resistance to B-lactam antibiotics in gram-negative bacteria (GNB). They are enzymes that hydrolyze older B-lactam antibiotics as well as broad-spectrum cephalosporins and monobactams.

Jacoby G A., (1994), in his paper "Genetics of extended-spectrum beta-lactamases" described that bacteria have adapted resistance to aztreonam, cefotaxime, ceftazidime, ceftriaxone and other oxyimino-beta-lactams, by altering existing plasmid-mediated class A and class D beta-lactamases.

Niemeyer D M., (1994), in his paper, "Regulation of beta-lactamase induction in gram-negative bacteria: a key to understanding the resistance puzzle," discusses that infections caused by drug-resistant microorganisms have posed a medical challenge since the advent of antimicrobial therapy. With the emergence of resistant strains, new antibiotics were available and introduced with great success until this decade. The appearance of multiresistant microorganisms poses a real and immediate public health concern.

Danziger L H. and Pendland S L, (1995) in their paper, "Bacterial resistance to beta-lactam antibiotics." have found that the most commonly prescribed antimicrobials in the United States are the beta-lactam antibiotics, and the most common mechanism of bacterial resistance to these agents is inactivation by beta-lactamase.

Medeiros A A., (1997), in his research paper, "Evolution and dissemination of beta-lactamases accelerated by generations of beta-lactam antibiotics," has stated that beta-lactamases are the principal mechanism of bacterial resistance to beta-lactam antibiotics.

Ritter E., et al, (1992) in their paper (article in German) "Outbreak of a nosocomial infection of SHV2-beta-lactamase-containing *Klebsiella pneumonia* strains in an operative intensive care unit." stated that resistant strains of *Klebsiella pneumoniae* produced type SHV2-broad-spectrum betalactamase. Thus, the bacteria were resistant to third-generation cephalosporins, such as cefotiam, cefotaxime and ceftriaxone and also to aminoglycosides and acylaminopenicillins.

S. J. Cavalieri, et al, (1991) in their paper, "Influence of beta-lactamase inhibitors on the potency of their companion drug with organisms possessing class I enzymes," undertook a study which was designed to assess the ability of sulbactam and clavulanate to induce beta-lactamases in two strains each of *Enterobacter cloacae, Citrobacter freundii, Serratia marcescens*, and *Pseudomonas aeruginosa* both in vitro and in vivo. The data suggest that beta-lactamase inhibitors can influence the in vivo potency of their companion drug.

Ghatole M., et al, (2004), in their paper, "Correlation of extended spectrum beta-lactamases production with cephalosporin resistance in gram negative *bacilli*", discussed that beta-lactamase production is an important mechanism of developing resistance to beta lactam group of antibiotics. Cephalosporins with extended spectrum of activity and stability were introduced to overcome this resistance, but soon production of extended spectrum beta lactamase (ESBLs), which are inducible in nature was reported.

Lopez-Hernandez S. et al, (1999) in their paper, "In vitro activity of beta-lactam agents and beta-lactamase inhibitors in clinical isolates of *Acinetobacter baumannii*", compared the in vitro activity of betalactam agents, (ampicillin, piperacillin and ticarcillin), betalactamase inhibitors (clavulanic acid, sulbactam and tazobactam) alone and in combination with betalactam agents (amoxicillin-clavulanic acid, ampicillin-sulbactam, piperacillin-tazobactam and ticarcillin-clavulanic) against 156 clinical isolates of *A. baumannii*. Sulbactam was the only betalactamase inhibitor which showed good in vitro activity, with a low MIC (50) and MIC (90) (and 32 mg/l, respectively) similar to ampicillin/sulbactam (2 and 16 mg/l, respectively). Sulbactam could be good therapeutic alternative for the treatment of multiresistant *A. baumannii* infections.

Sadar H S., et al, (2000) in their paper, "Comparative evaluation of the in vitro activity of three combinations of beta-lactams with beta-lactamase inhibitors: piperacillin/tazobactam, ticarcillin/clavulanic acid and ampicillin/sulbactam", found that ticarcillin/clavulanic acid was active against 85.8% of the Enterobacteriaceae, while ampicillin/sulbactam inhibited 83.2% of the samples.

Finegold S M, (1999) in his paper, "In vitro efficacy of beta-lactam/beta-lactamase inhibitor combinations against bacteria involved in mixed infections", found that the mixed infections are usually caused by a relatively limited range of bacteria, with the anaerobes and opportunistic pathogens contributing to their severity. In order to make the best therapeutic choice for a patient with a life-threatening infection, which is probably of mixed etiology, clinicians must be aware of the organisms that are likely to be involved, and the fact that most of them will produce beta-lactamase. Of the options available for empiric therapy, the beta-lactam/beta-lactamase inhibitor combinations represent a good choice. Their antibacterial spectra include both aerobic and anaerobic pathogens.

It is clear that there is a need to provide an inexpensive antibiotic formulation that will be effective against the increasing variety of beta lactamase-producing bacterial strains. There is also a need for such formulations to be provided in parenterally administrable form. There is also a need to develop antibiotic formulations that will not lead to rapid emergence of resistant bacterial strains.

OBJECTS AND ADVANTAGES OF THE PRESENT INVENTION

Accordingly, the objects and advantages of the present invention are described as below:

An object of the present invention is to provide an antibiotic formulation effective against beta lactamases-producing bacterial strains.

Another object of the present invention is to provide antibiotic formulation against beta lactamases-producing bacterial strains in parenterally administrable forms.

Yet another object of the present invention is to develop antibiotic formulations that does not lead to rapid emergence of resistant bacterial strains.

A still further object of the present invention is to provide therapeutically safe dose through a process of making antibiotic formulations effective against beta lactamase.

Another object of present invention is to enhance the total bactericidal range of existing ceftriaxone sodium injection.

SUMMARY OF THE INVENTION

The invention describes a composition for combating beta-lactamase-mediated antibiotic resistance using beta-lactamase inhibitor useful for injection, capable of pharmaceutical application.

The invention relates to pharmaceutical composition containing ceftriaxone (normally as ceftriaxone sodium) and sulbactam (normally as sulbactam sodium). Such compositions are found to be useful for intramuscular or intravenous administration as antibiotics for hospitalized patients with serious infections specifically due to beta lactamase producing bacterial strains. This invention relates to a pharmaceutical composition further including an aminocarboxylic acid chelating agent, for example, ethylenediaminetetraacetic acid (EDTA), or a pharmaceutically acceptable salt thereof. The pharmaceutical compositions of this invention have been found normally to enhance resistance to particulate formation in solutions to be administered parenterally. The invention also gives details of the dosage forms stored in sealed containers to be reconstituted before use. The invention also gives a process to manufacture these compositions. The invention gives a method of treating a subject having a condition or disorder, wherein a treatment with ceftriaxone sodium and/or sulbactam sodium is indicated.

DETAILED DESCRIPTION OF THE INVENTION

The present invention provides formulations containing ceftriaxone (or a pharmaceutically acceptable salt thereof, referred to hereafter as 'a ceftriaxone salt', such as ceftriaxone sodium) and sulbactam (or a pharmaceutically acceptable salt thereof, referred to hereafter as 'a sulbactam salt', such as sulbactam sodium) that can be used in the treatment of moderate to severe infections caused by ceftriaxone resistant beta-lactamase-producing strains of microorganisms which are made susceptible by the addition of sulbactam in conditions such as lower respiratory tract infections, acute bacterial otitis media, skin and skin structure infections, urinary tract infections (complicated and uncomplicated), pelvic inflammatory disease, bacterial septicemia, bone and joint infections, intra-abdominal infections, meningitis, surgical prophylaxis and pre-post operatively.

The different embodiments of the present invention are described below in detail. This invention basically provides a composition for combating beta-lactamase-mediated antibiotic resistance using beta-lactamase inhibitor, useful for injection, capable of pharmaceutical application, comprising:
  (a) ceftriaxone or a pharmaceutically acceptable salt thereof, and
  (b) sulbactam or a pharmaceutically acceptable salt thereof, in predetermined weight ratios.

It is desirable to minimize the particulate formations that occur in the pharmaceutical compositions upon reconstitution. The particulates consist of mobile, randomly sourced, extraneous substances other than gas bubbles, that cannot be quantified by chemical analysis due to small amount of material and due to its heterogeneous composition. Particulate inhibitors such as an aminocarboxylic acid chelating agent is optionally used in the present invention. Surprisingly it has been found by the inventor that their incorporation reduces the particulate formation in the reconstituted formulation. The optional chelating agent is selected from a group comprising ethylene diamine tetraacetic acid (EDTA) and salts thereof, diethylene triamine pentaacetic acid (DTPA), hydroxyethylene diamine triacetic acid (HEDTA), nitrilo triacetic acid (NTA) or a pharmaceutically acceptable salt thereof (normally as a sodium salt). The preferred chelating agent is EDTA and salts thereof, preferably edetate disodium as defined in the United States Pharmacopoeia, that can be used with this embodiment. In the reconstituted form, the amount of EDTA used in this embodiment is in the range of about 0.002 mg/ml to about 10 mg/ml, or more preferably, in the range of 0.003 to 2 mg/ml.

This composition further comprises a pharmaceutically acceptable tonocity adjusting agent, thereby rendering the composition physiologically isotonic.

In this composition the predetermined weight ratio of the ceftriaxone or of the pharmaceutically acceptable salt thereof, to the sulbactam or to the pharmaceutically acceptable salt thereof, is in the range from about 4:1 to about 1:4 respectively, preferably in the range from about 3:1 to about 1:3 respectively, more preferably in the range from about 2:1 to about 1:2 respectively.

The pharmaceutically acceptable salt of ceftriaxone is sodium salt thereof, such as ceftriaxone sodium.

The ceftriaxone sodium is (6R,7R)-7-[2-(2-amino-4-thiazolyl)glyoxylamido]-8-oxo-3-[[(1,2,5,6-tetrahydro-2-methyl-5,6-dioxo-as-triazin-3-yl)thio]methyl]-5-thia-1-azabicyclo[4.2.0]oct-2-ene-2-carboxylic acid, $7^2$-(Z)-(O-methyloxime), disodium salt, sesquaterhydrate which is in the form of white to yellowish-orange crystalline powder, the powder being readily soluble in water, sparingly soluble in methanol and very slightly soluble in ethanol.

The ceftriaxone sodium has tapped density in the range from about 0.5 g/ml to 0.6 g/ml and moisture content is in the range from about 8% to about 11% w/w, of the compound.

The pH of solution of the ceftriaxone sodium is in the range from about 6 to about 8, where the solution contains one part of the compound in 10 parts, of solution.

In this composition the pharmaceutically acceptable salt of the sulbactam is sodium salt thereof, such as sulbactam sodium.

The sulbactam sodium is sodium (2S,5R)-3,3-dimethyl-7-oxo-4-thia-1-azabicyclo(3.2.0) heptane-2-carboxylate 4,4-dioxide which is in the form of white to off-white dry powder for reconstitution, this powder of the sulbactam being freely soluble in water or dilute acids, sparingly soluble in acetone, ethyl acetate or chloroform.

The moisture content of the sulbactam sodium is less than about 1% w/w of the compound.

The particulate formation inhibitor comprises at least one compound selected from the group of ethylene diamine tetraacetic acid (EDTA), diethylene triamine penta-acetic acid (DTPA), hydroxyethylene diamine triacetic acid (HEDTA), nitrilo triacetic acid (NTA), and the pharmaceutically acceptable salts of any of these compounds, preferably sodium salts.

This particulate formation inhibitor is preferably the EDTA.

The composition of invention is a sterile blend of the ceftriaxone sodium and the sulbactam sodium optionally with particulate formation inhibitor.

The sterile blend comprises the ceftriaxone sodium and the sulbactam sodium in weight ratios in the range of about 4:1 to about 1:4 respectively, preferably from about 3:1 to about 1:3 respectively and more preferably from about 2:1 to 1:2 respectively.

The reconstituted solution of the composition of invention has pH in the range from about 5 to 8.

The tonocity adjusting agent mentioned earlier is either sodium chloride or dextrose which may be pre-blended with the composition or may be used during reconstitution or at the time of infusion.

The total sodium content of the ceftriaxone sodium and the sulbactam sodium is in the range from about 16.5 mg (0.719 mEq) to about 264.6 mg (11.48 mEq) of sodium.

The EDTA is present in the range from about 0.002 mg/ml to about 10 mg/ml of solution after reconstitution, and preferably the EDTA is in the range from about 0.003 mg/ml to about 2 mg/ml of solution after reconstitution.

According to yet another embodiment of the present invention, the required amount of the pharmaceutical composition disclosed herein is provided in a sealed airtight container which is selected from, a group comprising a vial, an ampoule, a syringe, a packet, a pouch and an auto-injector. These containers can contain the compositions disclosed in this invention in volumes of a single dose or in volumes of multiple doses up to 10. The interior space of the sealed airtight container comprises a fill volume occupied by the formulation of the present invention and a headspace volume occupied aseptically by an inert-gas-limited micro-atmosphere, which micro-atmosphere comprises essentially of one or more inert gases selected from the group consisting of noble gases and nitrogen, such that the ratio of the fill volume to headspace volume is not less than 1:1.

The pharmaceutically effective dosage of the composition, in the form of the concentrate of the dose, is provided in a sealed airtight container, wherein the container has a head space volume sufficient for introduction of appropriate volume of an aqueous solvent/compatible diluent selected from a group of sterile water for injection, bacteriostatic water for injection and isotonic sterile sodium chloride solution sufficient to form an appropriate reconstituted solution of the composition.

In case of unit/multiple dose of the composition, the pharmaceutically effective dose is provided in a sealed airtight container, wherein the container has a head space volume sufficient for introduction of appropriate volume of an aqueous solvent. Unit/multiple dose is in the form of an appropriate reconstituted solution of the composition.

For use as an injection, the composition is provided in the form of a sterile dry powder, in a sealed airtight container, to form a pharmaceutically acceptable required fixed dose combination for reconstitution prior to intramuscular or intravenous administration for the treatment of the bacterial infections.

As another alternative, the composition is provided in a sealed container such as transparent glass vial capped with appropriate halogenated stopper and seal, and is used for reconstitution for intramuscular or intravenous administration for the treatment of the bacterial infections.

When the composition is provided in a reconstituted form in a sealed airtight container, the interior space of the container comprises a fill volume occupied by the composition in reconstituted form and a head space volume occupied aseptically by an inert-gas-limited micro atmosphere, which comprises essentially one or more inert gas as selected from the group consisting of noble gases and nitrogen, preferably nitrogen, volume of the nitrogen gas being not more than 5% of the head space volume, and wherein ratio of said fill volume to the head space volume is not less than 1:1.

As one alternative, the ceftriaxone sodium and the sulbactam sodium are present in pharmaceutically effective single unit dose, in the sealed container.

As another alternative the ceftriaxone sodium and sulbactam sodium are present in pharmaceutically effective amount corresponding to about 1 to about 10 unit doses, in the sealed container.

It should be noted that this composition is filled in the sealed container aseptically under inert gas blanket.

This invention also provides a method of treating a subject, having a condition or disorder, wherein a treatment with ceftriaxone sodium and/or sulbactam sodium is indicated, which method comprises parenterally administering therapeutically effective amount of the composition.

This invention also provides a method of treatment or control of bacterial infections in mammals, comprising a therapeutically effective amount of composition.

As one alternative the composition comprises:
(a) the ceftriaxone or the pharmaceutically acceptable salt thereof, is present in an amount of about 2 g, calculated as ceftriaxone free acid,
(b) the sulbactam or the pharmaceutically acceptable salt thereof, is present in an amount in the range from about 1 g to about 2 g, calculated as sulbactam free acid,
(c) the composition further comprises optionally an amount of about 2 mg of EDTA, and
(d) the composition being reconstituted with about 20 ml of water for injection.

In this composition the total amount of sodium content of the ceftriaxone sodium and the sulbactam sodium is about 264.6 mg with 11.48 mEq of sodium.

As another alternative, the composition comprises:
(a) the ceftriaxone or said pharmaceutically acceptable salt thereof, is present in an amount of about 1 g, calculated as ceftriaxone free acid,
(b) the sulbactam or said pharmaceutically acceptable salt thereof, is present in an amount in the range from about 0.5 g to about 0.1 g, calculated as sulbactam free acid,
(c) the composition further comprises optionally an amount of about 1 mg of EDTA, and
(d) the composition being reconstituted with about 10 ml of water for injection.

In this composition the amount of sodium content of the ceftriaxone sodium and the sulbactam sodium is about 132.3 mg with 5.74 mEq of sodium.

As still another alternative, the composition comprises:
(a) the ceftriaxone or said pharmaceutically acceptable salt thereof, is present in an amount of about 0.5 g, calculated as ceftriaxone free acid,
(b) the sulbactam or said pharmaceutically acceptable salt thereof, is present in an amount in the range from about 0.25 g to about 0.5 g, calculated as sulbactam free acid, (c) the composition further comprises optionally an amount of about 0.5 mg of EDTA, and
(d) the composition being reconstituted with about 5 ml of water for injection.

In this composition the total amount of sodium content of the ceftriaxone sodium and the sulbactam sodium is about 66.15 mg with 2.87 mEq of sodium.

As further alternative, the composition comprises:
(a) the ceftriaxone or the pharmaceutically acceptable salt thereof, is present in an amount of about 0.25 g, calculated as ceftriaxone free acid,
(b) the sulbactam or the pharmaceutically acceptable salt thereof, is present in an amount in the range from about 0.125 g to about 0.25 g, calculated as sulbactam free acid,
(c) the composition further comprises optionally an amount of about 0.25 mg of EDTA, and
(d) the composition being reconstituted with about 4 ml of water for injection.

In this composition the total amount of sodium content of the ceftriaxone sodium and the sulbactam sodium is about 33.075 mg with 1.435 mEq of sodium.

As yet further alternative, the composition comprises:
(a) the ceftriaxone or the pharmaceutically acceptable salt thereof, is present in an amount of about 0.125 g, calculated as ceftriaxone free acid,
(b) the sulbactam or the pharmaceutically acceptable salt thereof, is present in an amount in the range from about 0.0625 g to about 0.125 g, calculated as sulbactam free acid,
(c) the composition further comprises optionally an amount of about 0.125 mg of EDTA, and
(d) the composition being reconstituted with about 2 ml of water for injection.

In this composition the total amount of sodium content of the ceftriaxone sodium and the sulbactam sodium is about 16.535 mg with 0.717 mEq of sodium.

For parenteral administration, the composition is in the form of sterile powder, which is reconstituted by addition of a compatible diluent selected from a group of sterile water for injection, bacteriostatic water for injection and isotonic sterile sodium chloride solution, prior to parenteral.

This invention also provides a process for preparing a composition for combating beta-lactamase-mediated antibiotic resistance using beta-lactamase inhibitors useful for injection, suitable for pharmaceutical application, comprising the steps of:
(a) sterile filling/blending two active ingredients, first active ingredient being the ceftriaxone or the pharmaceutically acceptable salt thereof and second ingredient being the sulbactam or the pharmaceutically acceptable salt thereof, optionally adding a particulate formation inhibitor (EDTA) or a pharmaceutically acceptable salt thereof and/or tonocity adjusting agent, the sterile filling/blending being continued for a period ranging from about 1 hour to about 4 hours,
(b) proportioning the sterile fill/blend of step (a), aseptically to get desired dose in weight ratio of said first active ingredient to said second active ingredient in the range from about 4:1 to about 1:4 respectively, preferably from about 3:1 to about 1:3 respectively, more preferably in the range of about 2:1 to about 1:2 respectively, and
(c) capping aseptically with pre-post inert gassing.

While the above description contains many specificities, these should not be construed as limitations in the scope of the invention but as exemplifications of embodiments thereof. Many other variations are possible. Accordingly, the scope of the invention should be determined not by the embodiments illustrated, but by the appended claims and their legal equivalents.

I claim:

1. A single unit premix pharmaceutical composition comprising
(a) Ceftriaxone or a pharmaceutically acceptable salt thereof and Sulbactum or a pharmaceutically acceptable salt thereof in a weight ratio of 2:1 to 4:1;
(b) EDTA or a pharmaceutically acceptable salt thereof in a range of about 0.6 milligrams per milliliter (mg/ml) to about 2.9 mg/ml of the reconstituted composition; and
(c) a total sodium content in a range of about 16.5 mg to about 264.6 mg or about 0.719 milliequivalents (mEq) to about 11.48 mEq., wherein said composition is present in a dry powder form suitable for parenteral administration after reconstitution.

2. The composition according to claim 1, wherein:
(a) said Ceftriaxone comprises ceftriaxone sodium;
(b) said Sulbactum comprises sulbactam sodium; and
(c) said EDTA comprises a disodium salt.

3. The composition according to claim 2, wherein the composition comprises:
(a) 2 grams (g) of ceftriaxone sodium, calculated as ceftriaxone free acid;
(b) 1 g of sulbactam sodium, calculated as sulbactam free acid; and
(c) wherein the composition, reconstituted with about 20 ml of an aqueous solvent, has a total amount of sodium content of about 264.6 mg of sodium or about 11.48 mEq of sodium.

4. The composition according to claim 2, wherein the composition comprises:
(a) 1 g of ceftriaxone sodium, calculated as ceftriaxone free acid;
(b) 0.5 g of sulbactam sodium, calculated as sulbactam free acid; and
(c) about 1 mg of EDTA; and
(d) wherein the composition, reconstituted with about 10 ml of an aqueous solvent, has a total amount of sodium content of about 132.3 mg of sodium or about 5.74 mEq of sodium.

5. The composition according to claim 2, wherein the composition comprises:
(a) 0.5 g ceftriaxone sodium, calculated as ceftriaxone free acid;
(b) 0.25 g sulbactam sodium, calculated as sulbactam free acid; and
wherein the composition, reconstituted with about 5 ml of an aqueous solvent, has a total amount of sodium content of about 66.15 mg of sodium or about 2.87 mEq of sodium.

6. The composition according to claim 2, the composition comprises:
(a) 0.25 g ceftriaxone sodium, calculated as ceftriaxone free acid;
(b) 0.125 g sulbactam sodium, calculated as sulbactam free acid; and
wherein the composition, reconstituted with 4 ml of an aqueous solvent, has a total amount of sodium content of about 33.075 mg of sodium or about 1.435 mEq of sodium.

7. The composition according to claim 2, wherein the composition comprises:
(a) 0.125 g ceftriaxone sodium, calculated as ceftriaxone free acid;

(b) 0.0625 g sulbactam sodium, calculated as sulbactam free acid; and wherein the composition, reconstituted with 2 ml of an aqueous solvent, has a total amount of sodium content of about 16.535 mg of sodium or about 0.717 mEq of sodium.

8. A composition as claimed in any of claims 1 to 7, packed and sealed in a sterile container under a blanket of inert gas, where the container is a vial, an ampoule, a syringe, a packet, a pouch, an auto injector, or combinations thereof, and wherein the interior space of the container comprises a fill volume occupied aseptically by an inert gas limited microatmosphere, which comprises one or more inert gases selected from a group consisting of noble gases and nitrogen; wherein if nitrogen is used, volume of the nitrogen gas being not more than 5% of the head space volume, and wherein ratio of the fill volume to the head space volume is no less than 1:1.

9. The composition according to claim 1, further comprising a sterile isotonic solution selected from the group consisting of sterile sodium chloride and dextrose, wherein the sterile isotonic solution is one of pre-blended with the composition, used during reconstitution, or used at the time of intravenous infusion.

* * * * *

UNITED STATES PATENT AND TRADEMARK OFFICE
CERTIFICATE OF CORRECTION

PATENT NO. : 8,273,732 B2
APPLICATION NO. : 11/720710
DATED : September 25, 2012
INVENTOR(S) : Manu Chaudhary It is certified that error appears in the above-identified patent and that said Letters Patent is hereby corrected as shown below:

Column 8, lines 6 to 18, cancel the text beginning with "1. A single unit" to and ending "after reconstitution." and insert the following claim:

--1. A single unit premix pharmaceutical composition comprising
(a) Ceftriaxone or a pharmaceutically acceptable salt thereof and Sulbactum or a pharmaceutically acceptable salt thereof in a weight ratio of 2:1 to 4:1;
(b) EDTA or a pharmaceutically acceptable salt thereof in a range of about 2.9 milligrams per milliliter (mg/ml) to about 10 mg/ml of the reconstituted composition; and
(c) a total sodium content in a range of about 16.5 mg to about 264.6 mg or about 0.719 milliequivalents (mEq) to about 11.48 mEq., wherein said composition is present in a dry powder form suitable for parenteral administration after reconstitution.--

Column 8, lines 33 to 43, cancel the text beginning with "4. The composition" to and ending "mEq of sodium." and insert the following claim:

--4. The composition according to claim 2, wherein the composition comprises:
(a) 1 g of ceftriaxone sodium, calculated as ceftriaxone free acid;
(b) 0.5 g of sulbactam sodium, calculated as sulbactam free acid; and
(c) wherein the composition, reconstituted with about 10 ml of an aqueous solvent, has a total amount of sodium content of about 132.3 mg of sodium or about 5.74 mEq of sodium.--

Signed and Sealed this
Twenty-sixth Day of February, 2013

Teresa Stanek Rea
*Acting Director of the United States Patent and Trademark Office*